United States Patent [19]

Henson

[11] Patent Number: 5,045,062
[45] Date of Patent: Sep. 3, 1991

[54] NON-REUSABLE HYPODERMIC SYRINGE WITH TURBINE ACCUATED FLOW CESSATION MEMBER

[76] Inventor: Jerry H. Henson, 4774 Annistown Rd., Stone Mountain, Ga. 30087

[21] Appl. No.: 377,055

[22] Filed: Jul. 10, 1989

[51] Int. Cl.⁵ ............................................. A61M 5/50
[52] U.S. Cl. .................................. 604/110; 604/207; 604/237
[58] Field of Search ............... 604/110, 186, 187, 199, 604/200, 207, 225, 236, 237, 241

[56] References Cited

U.S. PATENT DOCUMENTS

| | | | |
|---|---|---|---|
| 4,412,836 | 11/1983 | Brignola | 604/87 |
| 4,781,683 | 11/1988 | Wozniak et al. | 604/110 |
| 4,838,866 | 6/1989 | Marshall, Sr. | 604/152 |
| 4,857,061 | 8/1989 | Miller | 604/207 |
| 4,952,206 | 8/1990 | Ibanez e al. | 604/110 |

FOREIGN PATENT DOCUMENTS 2632190 12/1989 France .................................. 604/110
2218911 11/1989 United Kingdom ................ 604/110

Primary Examiner—John D. Yasko
Assistant Examiner—Adam J. Cermak
Attorney, Agent, or Firm—James B. Middleton

[57] ABSTRACT

A hypodermic syringe and needle includes a sealing mechanism to prevent reuse of the syringe by preventing the re-establishment of the flow of fluid after the passage of a predetermined quantity of fluid through the sealing mechanism. A fluid turbine is rotated by the fluid flow, and the turbine is carried by an actuator that moves along a threaded rod, the actuator carrying one part of a seal. After predetermined movement, the one part of a seal engages the other part of a seal and blocks fluid flow. While fluid is flowing, the seal parts are held apart for continued flow; but, on cessation of fluid flow, the seal parts engage and prevent subsequent fluid flow.

17 Claims, 2 Drawing Sheets

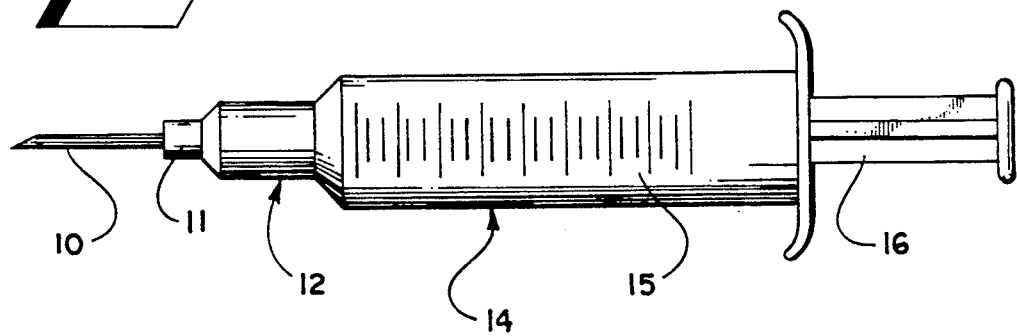
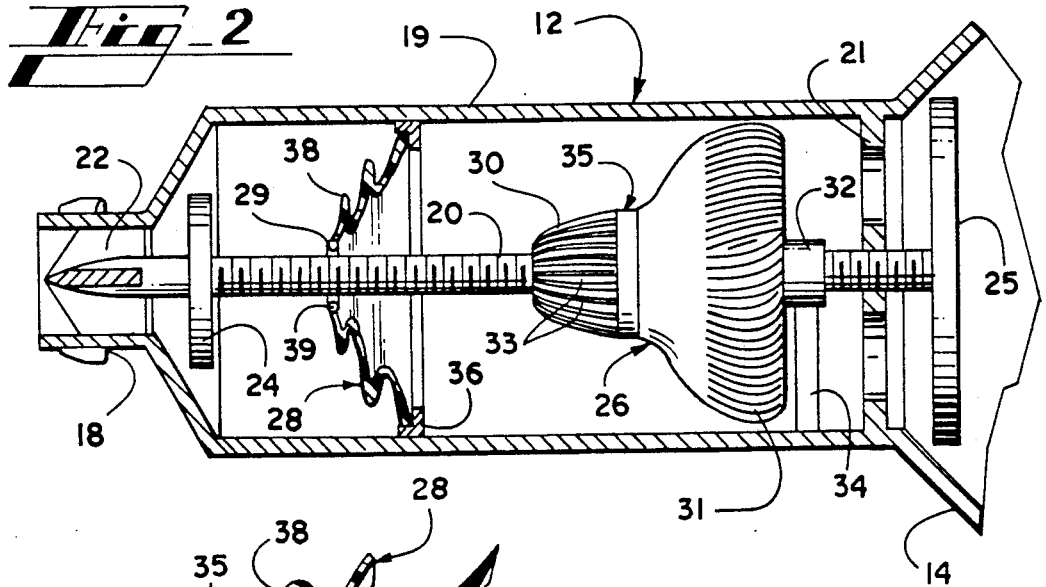
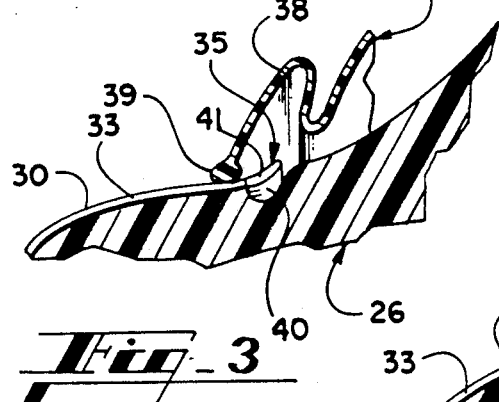
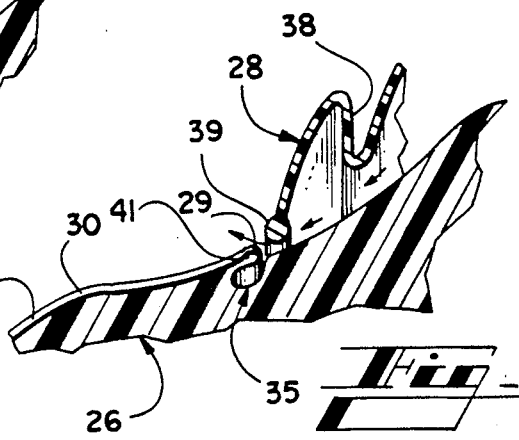

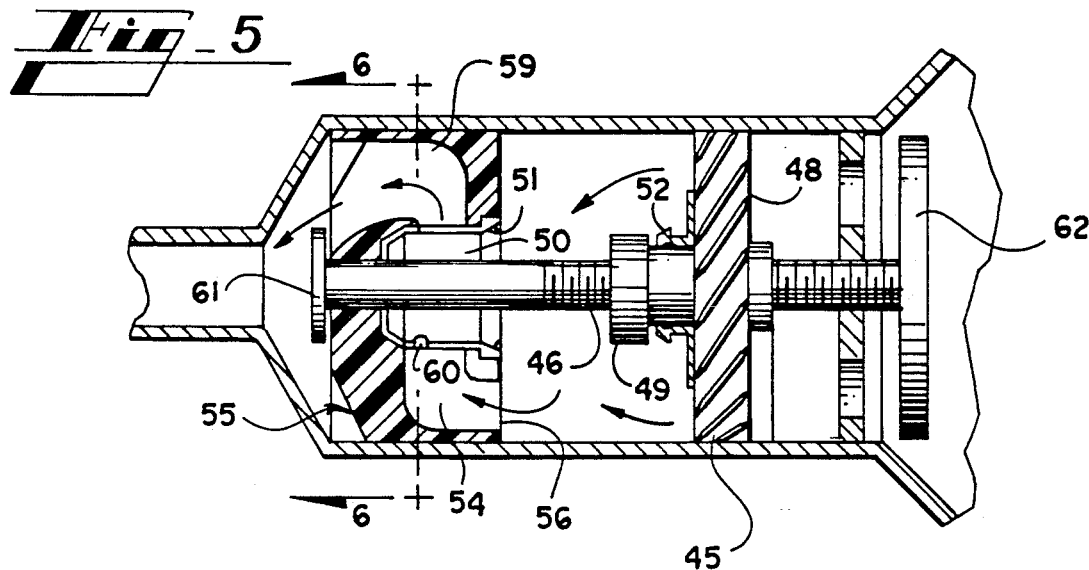
Fig_5
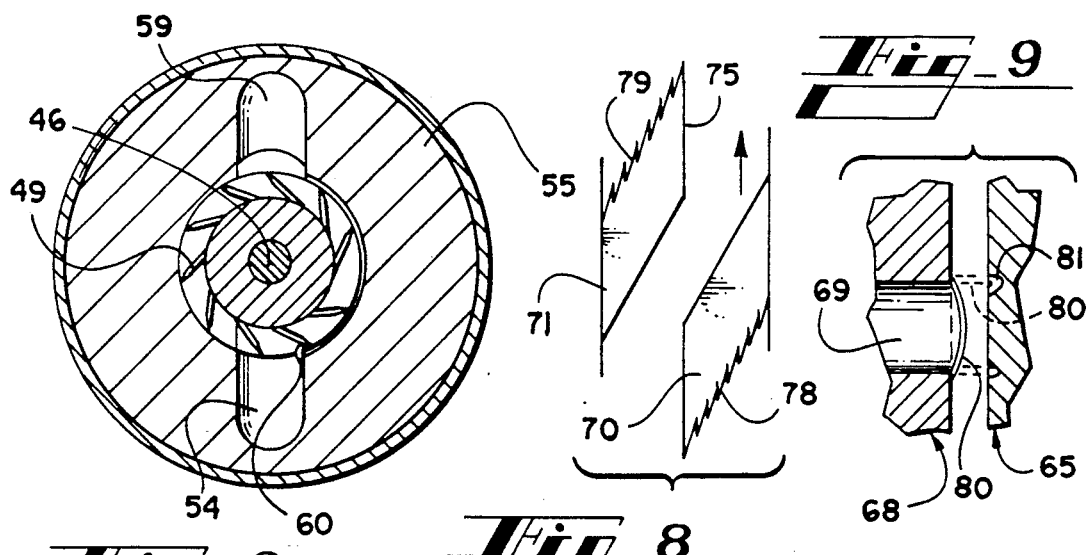
Fig_6
Fig_9
Fig_8
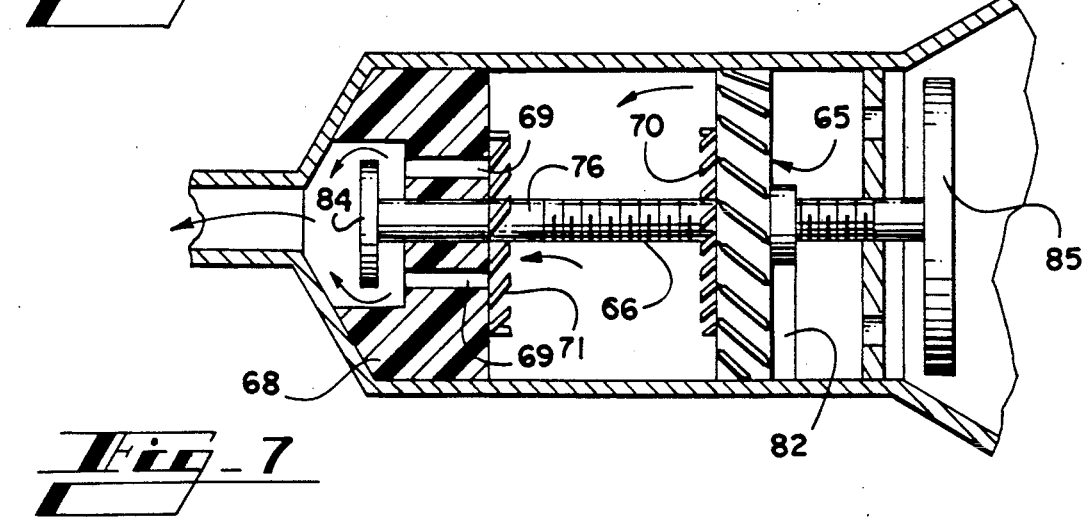
Fig_7

NON-REUSABLE HYPODERMIC SYRINGE WITH TURBINE ACCUATED FLOW CESSATION MEMBER

INFORMATION DISCLOSURE STATEMENT

It has been recognized that drug addicts share hypodermic needles and syringes. While such sharing is not particularly desirable from a hygienic point of view, the problem has been severely exacerbated by the AIDS virus. It is known that the AIDS virus is present in blood, and addicts who use drugs intravenously share a single syringe of the desired drug. In so doing, each person places the needle in a vein, draws enough blood to be sure of proper placement, then injects a portion of the drug in the syringe.

With the above outlined procedure, it will be obvious that a plurality of people are passing some of their blood with the syringe. The spread of AIDS and other diseases is therefore almost assured in such groups. To prevent these activities, it has been proposed to provide a hypodermic syringe that cannot be reused. There have been some efforts at providing a non-reusable syringe, but the prior art efforts have taken the direction of either destroying the syringe or locking the plunger after the plunger has been moved all the way forward. Other efforts have included means to prevent rearward motion of the plunger. Those skilled in the art will realize, however, that the plunger must be moved back and forth several times during the normal use of a syringe, and limiting motion to one direction will cause the syringe to be unusable. Destruction of the syringe at the end of a use will prevent further reuse, but it cannot solve the above stated problem of the shared needle and syringe. Furthermore, some of the prior art syringes require a deliberate effort at the end of plunger travel to force the plunger into the final movement that destroys the syringe or the plunger. Drug addicts are not likely to exert such intentional effort.

SUMMARY OF THE INVENTION

This invention relates generally to syringes, and is more particularly concerned with a single use hypodermic syringe having means for preventing the reestablishment of fluid flow after cessation of fluid flow, after a predetermined movement of the plunger.

The present invention provides, in conjunction with a generally conventional hypodermic needle and syringe, flow prevention means to prevent flow of fluid from the syringe to the needle. The flow prevention means allows a predetermined quantity of material to flow therethrough before the sealing mechanism becomes armed. Once the mechanism is armed, the apparatus is in position to prevent fluid flow, but established fluid flow can continue. When fluid flow ceases, the sealing mechanism becomes active and fluid flow cannot subsequently be re-established.

The apparatus of the present invention will therefore allow the several manipulations of the plunger required for normal, professional, use of a hypodermic syringe, and still allow the injection of the entire measured dose. Termination of injection before the full dose has been injected will actuate the sealing mechanism and the balance of the material cannot be injected.

BRIEF DESCRIPTION OF THE DRAWINGS

These and other features and advantages of the present invention will become apparent from consideration of the following specification when taken in conjunction with the accompanying drawings in which:

FIG. 1 is an elevational view of a hypodermic needle and syringe, and having a flow prevention means made in accordance with the present invention between the needle and the syringe;

FIG. 2 is a highly enlarged longitudinal cross-sectional view of the flow prevention means shown in FIG. 1 of the drawings;

FIGS. 3 and 4 are enlarged fragmentary, cross-sectional views showing the seal in the device of FIG. 2 for preventing fluid flow;

FIG. 5 is a view similar to FIG. 2 showing a modified form of the invention;

FIG. 6 is a cross-sectional view taken along the line 6—6 in FIG. 5;

FIG. 7 is a view similar to FIG. 2 showing another modified form of the invention; and, FIGS. 8 and 9 are enlarged, fragmentary views showing details of the device of FIG. 7.

DETAILED DESCRIPTION OF THE EMBODIMENTS

Referring now more particularly to the drawings and to those embodiments of the invention here chosen by way of illustration, FIG. 1 shows a hypodermic needle 10 having a fitting 11 for connection to a syringe or the like. The fitting 11 is here shown as fixed to a flow prevention means generally designated at 12, the flow prevention means being fixed to a generally conventional syringe 14 having a barrel 15 and a plunger 16. The flow prevention mean 12 is preferably formed integrally with the barrel 15, though it may be separately made and subsequently attached.

With the arrangement shown in FIG. 1 it will be readily understood that, if fluid cannot flow through the flow prevention means 12, fluid cannot flow from the syringe 14 to the needle 10. Once the flow prevention means 12 effectively seals against fluid flow, therefore, the syringe 14 becomes unusable.

For an understanding of the construction and operation of the flow prevention means 12, attention is directed to FIG. 2 of the drawings. In FIG. 2, the needle 10 is removed to show the connection 18, and the barrel 15 of the syringe 14 is broken away. The flow prevention means 12 is shown in cross-section to illustrate the construction.

The flow prevention means 12 includes a generally cylindrical casing 19 connected to the syringe 14 at one end and to a fitting 18 at the opposite end for receiving a needle or the like. Axially of the casing 19 there is a threaded rod 20, the rod 20 being appropriately supported by a web 21 at one end and a cross member 22 at the opposite end. The web 21 defines openings therethrough to allow fluid flow. The sealing mechanism of the flow prevention means is between the web 21 and the cross member 22. To protect this mechanism and prevent the intentional subversion of the mechanism, there are guard plates 24 and 25 at the ends of the rod 20. Due to the placement of these guard plates 24 and 25, instruments are prevented from entering the casing 19. This feature will be discussed in more detail hereinafter.

Looking at FIG. 2 of the drawings, the flow prevention means 12 includes an actuator 26 threadedly engaged with the threaded rod 20. The arrangement is such that rotation of the actuator 26 will cause the actuator to move along the rod 20 due to the inter-engagement of the threads. Concentrically mounted with the threaded rod 20, and forward of the actuator 26, there is a diaphragm 28. The diaphragm 28 defines a central opening 29 which will receive the forward portion 30 of the actuator 26. This engagement of the forward portion, or plug, 30 with the diaphragm 28 will, under certain circumstances, lock the mechanism so that the syringe is disabled.

The enlarged, rear portion 31 of the actuator 26 is formed as a fluid turbine, and it will be noted that the turbine 31 is sufficiently close to the wall of the casing 19 of the mechanism 12 that any fluid passing the turbine 31 of the actuator 26 will necessarily cause rotation of the actuator 26. Since the actuator 26 is threadedly engaged with the rod 20, any rotation of the actuator 26 will cause longitudinal movement of the actuator.

For the purpose of the present invention, it is desirable that the actuator 26 not move rearwardly, i.e. towards the syringe 14. The rearward motion may be prevented in many ways, including through the design of the turbine 31, and through the use of one-way clutches and the like. These and other arrangements will readily suggest themselves to those skilled in the art. For purposes of illustration, the actuator 26 has a rear hub 32 and a leaf 34 extending therefrom. The leaf 34 engages the inside of the wall 19 for allowing rotation in only one direction.

It will be noted that the forward surface of the actuator 26 is in the form of an ogive, the forward portion 30 being small and curving upwardly to the maximum diameter at the turbine 31. In the concave portion of the curve, there is a locking annulus generally indicated at 35. This locking annulus 35 will be discussed in more detail hereinafter.

Looking now at the diaphragm 28, it will be seen that the diaphragm is attached to the walls of the casing 19 by a ring 36. Extending inwardly from the ring 36, the diaphragm 28 is of a thin material that is elastic, and preferably has accordion folds such as the folds 38. The opening 29 is then bounded by a reinforcing rib 39.

With the above general description in mind, it should be realized that, when fluid flows from the syringe 14 into the flow prevention means 12, the fluid will pass the turbine 31 and cause rotational motion of the actuator 26. This rotational motion of the actuator will cause forward motion along the threaded rod 20. After a predetermined amount of such motion by the actuator 26, the forward portion 30 will engage the diaphragm 28. As the actuator 26 engages the diaphragm 28, the reinforcing ring 39 will stretch and allow the diaphragm to pass over the actuator 26, and the actuator will still be able to move forwardly as the actuator rotates. Ultimately, the locking annulus 35 will pass the reinforcing rib 39. At this point, fluid flow through the diaphragm 28 holds the diaphragm in a somewhat stretched condition to allow fluid flow to continue. If the fluid flow stops, the diaphragm 28 will contract to its normal, relaxed state and the reinforcing ring 39 will engage the locking annulus 35 and disable the syringe. The grooves 33 are provided to allow enough flow to prevent hydrostatic locking before the diaphragm seats in the locking annulus.

It will be understood that the integrity of the diaphragm 28 and of the actuator 26 are important to the proper operation of the flow prevention means 12. The guard plates 24 and 25 are arranged to prevent access to the diaphragm and the actuator without destroying the usefulness of the syringe. It will be seen that the guard plate 24 is placed so that an implement cannot be inserted through the fitting 18, past the plate 24 order to damage the diaphragm 28. Similarly, the guard plate 25 is arranged so that an implement cannot be passed through the syringe 14, past the guard plate 25 and into the flow prevention means 12 to damage the actuator 26.

Another possible means for disabling the flow prevention means is to create a hole in the side of the flow prevention means 12. If a small opening can be made through the wall 19, a pin or the like can be used to prevent rotation of the actuator 26. To prevent subversion in this manner, it is contemplated that the casing 19 will be made of a highly brittle substance. Those skilled in the art will understand that some types of steel can be made sufficiently brittle that efforts at puncturing the steel will cause severe cracking, to the point that the chamber will no longer be fluid tight. Also, there are plastic materials that can be made equally brittle so that an attempt to subvert the mechanism will result in destruction of the syringe.

Another possible technique for attempting to subvert the device of the present invention is to heat the device. Since at least some of the parts will probably be made of plastic, one might assume that the arming mechanism will be destroyed by heat. To prevent this form of subversion, one possibility is to be sure that the casing of the device melts at a lower temperature than the apparatus of the sealing mechanism. The sealing mechanism, and perhaps the syringe itself, could be designed to melt before the sealing mechanism is damaged.

Another technique is to cause the needle to be obstructed by heat. It is contemplated that a relatively low melting point material will be placed adjacent to the fitting 22. Heating of the device to subvert the mechanism will then cause the low melting point material to flow into the bore of the needle and render the needle useless. This last arrangement is shown in conjunction with other embodiments of the invention described below.

Attention is now directed to FIGS. 3 and 4 of the drawings which illustrate the locking of the diaphragm with the locking annulus to effect a seal. FIGS. 3 and 4 are fragmentary, highly enlarged views showing the locking annulus 35 and the reinforcing rib 39 of the diaphragm 28 as it moves in this vicinity. It will be seen that the locking annulus 35 includes a notch 40 in the actuator 26, the notch 40 being covered by a flap 41. With this arrangement, the reinforcing rib 39 can move from the forward portion 30, across the flap 41 so that no locking takes place. FIG. 4 of the drawings illustrates the condition wherein the actuator 26 has moved forward to the point that the reinforcing rib 39 is rearwardly of the locking annulus 35; however, as indicated by the arrows, there is continued fluid flow, assisted by the grooves 33, to hold the diaphragm away from the actuator 26. As a result, the diaphragm cannot stop the fluid flow. As the device is shown in FIG. 4, it will be readily understood that, once fluid flow ceases, the natural elasticity of the diaphragm 28, and particularly the reinforcing rib 39, will contract to lie very snugly against the actuator 26. Because of the slope of the actuator 26, and the elasticity of the now-stretched rib 39, the rib 39 will tend to move towards the forward portion 30 of the actuator 26. In this direction, it will be noted that the flap 41 will lift to allow the rib 39 to enter the notch 40. Once the rib 39 is within the notch 40, the syringe side of the chamber will be completely isolated from the needle side of the chamber. The actuator 26 can no longer move forward, and of course cannot move rearwardly.

Attention is now directed to FIG. 5 of the drawings which shows a modified form of sealing mechanism. This sealing mechanism includes an actuator 45 threadedly engaged with an axially extending rod 46. As in the previously described embodiment, the actuator 45 includes turbine blades 48 for causing rotation of the actuator when fluid passes the actuator 45. Thus, as in the previously described embodiment, flow of fluid through the chamber will cause rotation of the actuator 45 and will cause the actuator 45 to move into sealing position.

The means for effecting a seal in this embodiment includes a rotor 49 rotatably carried by the actuator 45. The rotor 49 is sized to fit rather precisely into the housing 50. It will be noticed that, as the actuator 45 moves forward, towards the needle, the rotor 49 will be received within the housing 50. It should also be noticed that the housing 50 has a lip 51 which mates with a plug 52 on the actuator 45. The plug 52 is sized to mate with the lip 51 and prevent fluid flow therebetween. The plug 52 will also lock to the lip 51 when the two are joined.

When the plug 52 is engaged by the lip 51, the rotor 49 will be within the housing 50. The threads on the rod 46 terminate to allow the actuator 48 to rotate without jamming. There is a passageway 54 through the support 55, the passageway 54 extending from within the chamber to the entrance 56 of the housing 50. Opposite the entrance 56, the housing 50 defines an exit 58 which leads to an exit passageway 59 defined in the support 55.

At the entrance 56, there is a tab 60, the tab 60 being carried by the support 55 and extending inwardly to engage the vanes of the rotor 49 when the rotor is inserted into the housing 50. The tab 60 acts as a light spring, so rotation of the rotor 49 is allowed to continue, the tab bending easily so rotation is not stopped. Once rotation of the rotor 49 is stopped, however, the tab 60 is strong enough that rotation cannot be subsequently initiated.

Considering the description of the first embodiment, and the foregoing discussion of the embodiment shown in FIGS. 5 and 6, operation should be understood. As the plunger of the syringe is depressed, fluid will flow past the actuator 45, causing rotation of the actuator 45 and consequent movement along the rod 46. After a predetermined amount of fluid flow, the rotor 49 will be inserted into the housing 50, and the plug 52 will engage the lip 51. At this point, fluid must pass the turbine blades 48, and flow into the passageway 54. From the passageway 54, fluid will flow into the housing 50, thereby rotating the vanes of the rotor 49; then, the fluid exits through the passageway 59, and to the needle.

Once the rotor 49 is received within the housing 50, and the plug 52 is engaged with the lip 51, it will be understood that fluid must rotate the rotor 49 to pass through the sealing mechanism. The vanes of the rotor 49 fit closely enough within the housing 50 that no fluid flow can be established or maintained without rotation of the rotor. As the rotor 49 enters the housing 50, the rotor will begin to rotate. When the tab 60 engages the rotor 49, the rotor will already be rotating, and the rotation will be maintained. However, once the fluid flow stops, causing the rotor 49 to stop rotating, the tab 60 will hold the rotor 49 firmly enough that fluid flow cannot be restarted.

As in the previous embodiment, there are guard disks 61 and 62 at each end of the rod 46 to prevent the entry of a tool to subvert the sealing mechanism. Also, it is contemplated that the support 55 will be made of a low-melting-point thermoplastic. If the device is heated in an effort to subvert the mechanism, the material of the support 55 will melt and run into the needle to plug the bore in the needle.

Looking next at FIG. 7 of the drawings, the next embodiment of the invention includes an actuator 65 and an axially extending rod 66. A support 68 defines openings 69 therethrough. The sealing mechanism comprises seal portions on the support 68 and actuator 65, and locking means also on the support 68 and on the actuator 65.

Considering the sealing mechanism in more detail, the actuator 65 carries a plurality of angularly disposed teeth 70 extending therefrom. The teeth 70 are pointing in a direction opposite to the direction of rotation of the actuator. The support 68 carries a complementary plurality of angularly disposed teeth 71. The teeth 71 point in the opposite direction from the teeth 70, so the teeth in the two sets of teeth are parallel to one another. This is shown somewhat in FIG. 3 and is shown in detail in FIG. 8. FIG. 8 illustrates two of the teeth, one tooth 70 and one tooth 71. Thus, looking at FIGS. 7 and 8 it should be understood that, as in the previously described embodiment, the actuator 65 will rotate with fluid flow, and will move towards the support 68. When the teeth 70 and 71 engage, the teeth 70 will be rotating, so the adjacent surfaces 74 and 75 will contact. The teeth are formed of an elastic material so the teeth will bend somewhat under the pressure, but the teeth 70 will continue to move with respect to the teeth 71.

It will be noticed that the threads on the rod 66 end, leaving an area 76 devoid of threads. When the actuator 65 is in this area 76, the actuator will rotate without forward motion. However, when the actuator 65 stops rotating, the actuator cannot back up on the rod 66 because of the threads. The energy stored in the bent fingers will then tend to straighten the fingers, causing adjacent fingers to intermesh. As the fingers 70 and 71 overlap, the saw-tooth edges 78 and 79 will prevent release of the fingers, and the actuator 65 will be effectively locked to the support 68.

FIG. 9 shows the seal to prevent fluid flow when the actuator 65 and support 68 are locked together. The holes 69 are surrounded by a lip 80, and a groove 81 in the actuator 65 is located to receive the rib 80. Thus, when the actuator 65 and the support 68 meet, there will be a good seal to prevent fluid flow.

This embodiment of the invention also includes the ratchet strip 82 to limit rotation of the actuator 65, and guard plates 84 and 85 for mechanical protection of the sealing mechanism. As before, the support 68 will have a low melting point to plug the bore of the needle if the device is heated.

When a professional must use a hypodermic needle and syringe to give a shot, there is a series of necessary steps. First, the syringe is normally utilized to inject air into the medicine bottle. After the air has been injected, the plunger is pulled back to fill the syringe to the desired level, and generally to a point somewhat beyond the desired level. After the needle is removed from the medicine bottle, the plunger is pushed forward to a small extent to force some medicine out of the syringe and leave precisely the desired dosage in the syringe. The syringe is now ready to give the shot to the patient. For this procedure, the needle is inserted into the patient, and the plunger is retracted slightly to see if blood is withdrawn from the patient. If the medicine is an intravenous medicine, one is looking for blood to be sure the needle is placed within a vein. If the medicine is an intramuscular medicine, one needs to be sure there is no blood to indicate that the needle is planted in muscle tissue. If the needle is improperly placed, the needle must of course be withdrawn somewhat and the procedure repeated. Finally, the plunger is pushed inwardly until the full dose has been delivered from the syringe.

Because of the foregoing steps, it will be understood that a syringe must allow some back and forth motion of the plunger without disabling the syringe; however, if a large amount of back and forth motion is allowed, it may be sufficient for needle sharing and the intended safety is lost. The present invention resolves the difficulty by providing the actuator, which performs the function of a metering means. The device can be designed to allow a predetermined quantity of fluid to flow past the turbine of the actuator 26, 48 or 65 before the device is armed, and this quantity can be the amount required for the above described manipulations prior to giving a shot. Once the device is armed, the plunger can be moved forwardly to continue to expel medicine so long as delivery of medicine is not stopped. Once delivery is stopped, as in needle sharing, the sealing mechanism will lock to effect a seal, and the balance of the medicine will not be able to be dispensed from the syringe.

It will of course be understood by those skilled in the art that the particular embodiments of the invention here presented are by way of illustration only, and are meant to be in no way restrictive; therefore, numerous changes and modifications may be made, and the full use of equivalents resorted to, without departing from the spirit or scope of the invention as outlined in the appended claims.

I claim:

1. In the combination of a hypodermic needle and syringe, the improvement comprising flow prevention means between said needle and said syringe for selectively preventing the flow of fluid from said syringe to said needle, said flow prevention means including an enclosure, a sealing means within said enclosure including an actuator, a first seal portion carried by said actuator, a second seal portion within said enclosure and fixed with respect thereto, said actuator being selectively movable within said enclosure so that said first seal portion approaches said second seal portion, the arrangement being such that the flow of fluid through said enclosure prevents sealing between said first seal portion and said second seal portion, the further improvement wherein said actuator comprises a fluid turbine rotatable by the flow of fluid through said enclosure, a central rod extending through said enclosure, external threads on said rod, said actuator defining a threaded hole therethrough, said rod being received within said threaded hole and threadedly engaging said actuator, the arrangement being such that the flow of fluid past said actuator causes rotation of said actuator and consequent movement along said rod towards said second seal portion.

2. In the combination as claimed in claim 1, the further improvement wherein said actuator and said central rod constitute a flow meter for measuring the flow of fluid through said enclosure, said actuator moving to the position to place said first seal portion and said second seal portion in juxtaposition on flow of a predetermined amount of fluid.

3. In the combination as claimed in claim 2, said sealing means further including at least one guard plate, said guard plate being disposed at one end of said enclosure, and being positioned to prevent mechanical access to at least one of said first seal portion and said second seal portion.

4. In the combination as claimed in claim 3, said at least one guard plate being disposed adjacent to said syringe for preventing access to said actuator, said sealing means including a second guard plate disposed adjacent to said needle for preventing access to said second seal portion.

5. In the combination as claimed in claim 4, the improvement wherein said enclosure is constructed of a brittle material.

6. In the combination as claimed in claim 5, said actuator further including means for preventing movement of said actuator away from said second seal portion.

7. In the combination as claimed in claim 6, the improvement wherein said first seal portion comprises a tapered plug, and said second seal portion comprises a diaphragm defining a central opening, said central opening receiving said plug for stopping fluid flow.

8. In the combination as claimed in claim 7, said diaphragm being sufficiently elastic that the flow of fluid over said plug and through said central opening will prevent the stopping of fluid flow.

9. In the combination as claimed in claim 8, the improvement wherein said plug defines a locking annulus for receiving said diaphragm, the arrangement being such that, when said diaphragm enters said locking annulus fluid cannot flow through said central opening.

10. In the combination as claimed in claim 6, the improvement wherein said first seal portion includes a rotor rotatably carried by said actuator, said second seal portion includes a housing for receiving said rotor, said housing defining an entrance and an exit for allowing fluid to pass through said housing, the arrangement being such that said rotor must rotate to allow fluid to pass through said housing when said rotor is within said housing.

11. In the combination as claimed in claim 10, the further improvement including a flexible tab engaging said rotor, the arrangement being such that said rotor can continue to rotate but cannot be stopped and restarted with said tab engaging said rotor.

12. In the combination as claimed in claim 6, the further improvement including a support within said enclosure adjacent to said needle, said support defining openings therethrough for fluid flow, said second seal portion comprising a lip surrounding said openings, said first seal portion comprising a groove in said actuator for receiving said lip.

13. In the combination as claimed in claim 12, the improvement including locking means for locking said actuator to said support.

14. The method, for disabling a hypodermic syringe and needle for preventing reuse, including the steps of detecting fluid flow from the syringe towards the needle, moving an actuator in response to said fluid flow, said actuator carrying a first seal portion and being moved towards a second seal portion so that a predetermined quantity of fluid will flow from the syringe towards the needle before the device becomes armed, continuing to move said actuator until said first and second seal portions are adjacent so that the device is armed, and preventing sealing engagement of said seal portions by a continuous flow of fluid from said syringe to said needle.

15. The method as claimed in claim 14, and further including the step of holding said first seal portion away from sealing engagement with said second seal portion with continued fluid flow, and sealingly engaging and locking said seal portions on cessation of said fluid flow.

16. The method as claimed in claim 15, and further including the step of preventing motion of said actuator in a direction away from said second seal portion.

17. In the combination of a hypodermic needle and syringe, the improvement comprising flow prevention means between said syringe and said needle for selectively preventing flow of fluid from said syringe to said needle, said flow prevention means including an enclosure, a flow meter within said enclosure for determining when a predetermined quantity of fluid has passed through said flow prevention means, said flow meter including an actuator, a first seal portion carried by said actuator, a second seal portion within said enclosure and fixed with respect thereto, said actuator being movable within said enclosure during the flow of said predetermined quantity of fluid so that said first seal portion approaches said second seal portion, the arrangement being such that the constant flow of fluid through said enclosure prevents sealing between said first seal portion and said second seal portion when said first and second seal portions are adjacent to each other.

* * * * *